(12) United States Patent
Liu et al.

(10) Patent No.: US 8,143,064 B2
(45) Date of Patent: Mar. 27, 2012

(54) REAGENTS AND METHODS FOR CLASSIFYING LEUKOCYTES

(75) Inventors: Bing Liu, Shenzhen (CN); Wenjuan Xu, Shenzhen (CN); Xiangping Meng, Shenzhen (CN); Yanmei Qiao, Shenzhen (CN); Mulong Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 711 days.

(21) Appl. No.: 12/265,588

(22) Filed: Nov. 5, 2008

(65) Prior Publication Data
US 2009/0162830 A1 Jun. 25, 2009

(30) Foreign Application Priority Data

Dec. 24, 2007 (CN) .......................... 2007 1 0125463

(51) Int. Cl.
*G01N 33/48* (2006.01)
(52) U.S. Cl. .................. 436/10; 436/8; 436/17; 436/18; 436/63; 436/164; 436/166; 436/174; 436/175; 435/2; 252/408.1
(58) Field of Classification Search .............. 436/8, 10, 436/17, 18, 63, 164, 166, 174, 175; 435/2; 252/408.1
See application file for complete search history.

(56) References Cited

U.S. PATENT DOCUMENTS

| | | | | |
|---|---|---|---|---|
| 4,745,071 | A | * | 5/1988 | Lapicola et al. ............... 436/63 |
| 5,155,044 | A | | 10/1992 | Ledis et al. |
| 5,316,725 | A | | 5/1994 | Carver, Jr. et al. |
| 5,316,951 | A | | 5/1994 | Carver, Jr. et al. |
| 5,510,267 | A | | 4/1996 | Marshall |
| 5,538,893 | A | | 7/1996 | Sakata et al. |
| 5,618,733 | A | | 4/1997 | Sakata et al. |
| 5,677,183 | A | * | 10/1997 | Takarada et al. ............... 436/10 |
| 5,747,343 | A | * | 5/1998 | Tsuchiya et al. ............... 436/63 |
| 5,763,280 | A | * | 6/1998 | Li et al. ........................ 436/66 |
| 5,968,832 | A | * | 10/1999 | Uchihashi et al. .............. 436/10 |
| 7,465,584 | B2 | * | 12/2008 | Matsumoto et al. ............ 436/10 |
| 2007/0275469 | A1 | * | 11/2007 | Xu et al. ....................... 436/10 |

FOREIGN PATENT DOCUMENTS

| | | |
|---|---|---|
| CN | 88101677.2 | 1/1989 |
| CN | 1126836 A | 7/1996 |
| CN | 95115317.X | 7/1996 |
| CN | 101078720 A | 11/2007 |
| CN | 101078721 A | 11/2007 |

* cited by examiner

*Primary Examiner* — Maureen Wallenhorst
(74) *Attorney, Agent, or Firm* — Kory D. Christensen; Matthew S. Bethards; Stoel Rives LLP

(57) ABSTRACT

A reagent for classification of leukocytes includes (a) at least two cationic surfactants; (b) at least one organic compound bearing a hydrophobic group and an anionic group; (c) a buffer for adjusting pH into a range of approximately 2-8. Also disclosed is a method for classifying leukocytes with the reagent. With the reagent and method, erythrocytes are lysed rapidly and classification of leukocytes into five groups is achieved in the same channel. The reaction may be carried out at approximately between 10-40° C. and scattered light signals may be detected at two angles for measuring the classification of leukocytes into five groups.

18 Claims, 3 Drawing Sheets

REAGENTS AND METHODS FOR CLASSIFYING LEUKOCYTES

CROSS-REFERENCE TO RELATED APPLICATIONS

This application claims priority to Chinese Patent Application No. 200710125463.0, filed Dec. 24, 2007, for "REAGENTS AND METHODS FOR CLASSIFYING LEUKOCYTES," the disclosure of which is fully incorporated herein by reference.

TECHNICAL FIELD

The present disclosure is related to reagents and methods for classifying cells, and in particular, to reagents for classifying blood leukocytes and methods for classifying blood leukocytes with the reagents.

BRIEF SUMMARY

A reagent for classifying leukocytes into five groups corresponding to lymphocytes, monocytes, neutrophils, eosinophils, and basophils is disclosed.

BRIEF DESCRIPTION OF THE DRAWINGS

In FIGS. 1-5, 0 represents fragments, 1 represents lymphocytes, 2 represents monocytes, 3 represents neutrophils, 4 represents eosinophils, and 5 represents basophils.

DETAILED DESCRIPTION

Figure 1:
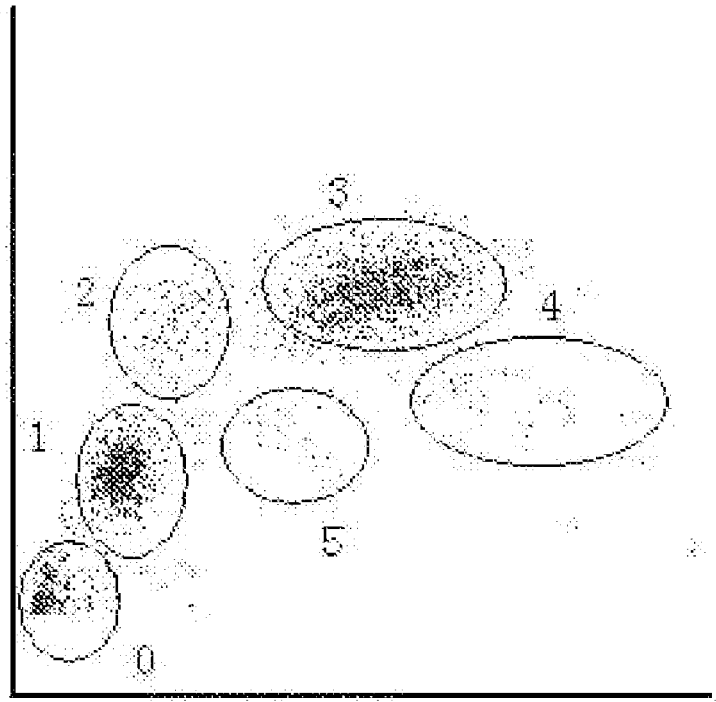
FIGS. 1-3 show the classification of leukocytes from three blood samples into five groups with one embodiment of a reagent for classification of leukocytes.

In clinical testing fields, it is desirable to classify and count leukocytes in the whole blood of patients to support the diagnosis and treatment of diseases.

Up to date, a number of devices and methods for classifying and counting leukocytes have been reported which classify and count leukocytes by the physical, electrical and optical features of the treated cells after the blood has been treated with a lytic or a staining agent.

For example, some of these methods classify leukocytes by detecting the fluorescence emitted by the leukocytes stained with a staining agent, while others achieve the classification of leukocytes by detecting the electrical signals or scattered light signals after the leukocytes have been particularly treated with a lytic agent.

CN 95115317.X discloses a method for classifying leukocytes into five groups with a reagent for classifying leukocytes into four groups together with a reagent for detecting basophils. The reagent for classifying leukocytes into four groups comprises at least one ionic surfactant, at least one negatively charged organic compound, a nonionic surfactant, and a buffer. It is used to treat a first blood sample to classify the blood cells into four groups: lymphocytes, monocytes, eosinophils, and basophils with neutrophils. The reagent for detecting basophils is used to treat a second blood sample to classify the basophils from others. By combining the results from both reagents, this method classifies leukocytes into five groups. The classification is detected by a two-angle laser light scattering method.

U.S. Pat. No. 5,677,183 proposes a method for classifying leukocytes into five groups and counting each group. The method employs a two-angle light scattering method with a reagent for classifying leukocytes into four groups and a reagent for detecting basophils. The reagent for classifying leukocytes into four groups comprises at least one ionic surfactant to lyse erythrocyte and damage the cell membrane of leukocytes, at least one negatively charged organic compound to bind with positively charged materials in the leukocytes to give morphological changes to the leukocytes, a nonionic surfactant and a buffer to adjust the pH value. The reagent for detecting basophils comprises at least one polyoxyethylene-type nonionic surfactant having a polymerization degree of 3-10, at least one cationic surfactant, and a buffer for adjusting the pH to 2.5-4.0. A first reagent is added to a first blood sample to classify leukocytes into four groups: lymphocytes, monocytes, eosinophils, and basophils with neutrophils. A second reagent is added to a second blood sample to classify the basophils from other leukocytes by morphological features and cell size information. By combining the results from both reagents, this method classifies leukocytes into five groups.

U.S. Pat. No. 5,618,733 discloses a reagent for classifying leukocytes into four groups comprising at least one ionic surfactant, either cationic or anionic, to simultaneously lyse erythrocyte and damage the cell membrane of leukocytes; at least one organic compound having an anion to bind with the cationic component in the leukocytes to give morphological differences among different groups of leukocytes; a nonionic surfactant; and a buffer to adjust the pH value. The measurement may be carried out with a two-angle laser light scattering method.

U.S. Pat. No. 5,747,343 proposes a method comprising: lysing erythrocytes in a short period of time with a reagent comprising at least an anionic or ampholytic surfactant while maintaining the original or approximately original morphology of leukocytes, and classifying the leukocytes into four groups by gathering the signals of both forward scattered light and side scattered light.

U.S. Pat. No. 5,155,044 proposes a method and a reagent system for rapid isolation and analysis of leukocytes from a whole blood sample. The hemolytic reagent system consists of a first reagent selected from formic acid, acetic acid and combination thereof and a second quenching reagent. The reagent lyses erythrocytes and creates subtle modifications to the leukocytes to enable the classification into five sub-populations. The advantage and uniqueness of this reagent system is the surprising speed at which it lyses the erythrocytes and the ability to further differentiate the leukocyte population. Following hemolysis, the quenching agent is added to retard further hemolysis and inhibit any further dramatic changes to the leukocyte population. The treated blood sample has retained its characteristic immunochemical response. The measurement may be carried out by a two-angle laser light scattering method, or a direct current (DC) method and a radio frequency (RF) method, or a direct current (DC) method and a light scattering method.

U.S. Pat. No. 5,510,267 discloses a hemolytic reagent and a method for classifying leukocytes into five groups. The hemolytic reagent comprises an aromatic oxyethanol, an organic buffering agent having a pK value of about 8.5, and a nonionic detergent. The blood sample is first mixed with a diluent solution, then the hemolytic reagent is added to lyse the erythrocytes while maintaining the light scattering features of leukocytes intact for at least 30 seconds, so as to classify the leukocytes into five groups by collecting the signals of scattered light at four angles.

CN 88101677.2 is a method for classifying leukocytes by lysing the erythrocytes with an acid lytic agent of pH 2.6-4 rapidly while maintaining the leukocytes intact and then followed by the addition of a quenching agent. The measurement may be carried out by light scattering or a direct current/radio frequency method.

There are a number of problems with the conventional methods disclosed. For example, by a two-angle light scattering method, U.S. Pat. Nos. 5,618,733 and 5,747,343 are capable of classifying leukocytes into four groups corresponding to lymphocytes, monocytes, neutrophils or eosinophils, but both fail to separate the basophils from others.

Additionally, CN 95115317.X and U.S. Pat. No. 5,677,183 achieve the classification of leukocytes into five groups by combining the results obtained in two channels using two reagents to separately treat two blood samples. U.S. Pat. No. 5,510,267 makes it possible to achieve the classification of leukocytes into five groups in one channel by detecting the scattered light signals at four angles, which complicates the equipment design and thus raises the equipment costs.

With regard to the classification techniques described in U.S. Pat. No. 5,155,044 and CN 88101677.2, it is possible to classify leukocytes into five groups in one channel merely at room temperature. With the changing of the ambient temperature, it is difficult to keep the temperature constant at 25° C. The measurements fluctuate with the temperature and thus hurt the measurement precision. Under the circumstances, a thermostatic apparatus is required to eliminate the influence of temperature change. In addition, to keep the temperature at 25° C., not only heating devices but also cooling devices, are necessary, significantly increasing the equipment costs.

The present disclosure provides a reagent system as well as a method for precisely classifying leukocytes into five groups within one channel at a broad range of temperature.

The present disclosure provides a reagent for classification of leucocytes into five groups, wherein the reagent includes:

(a) at least two cationic surfactants capable of lysing erythrocytes and partly damaging the cell membrane of leukocytes;

(b) at least one organic compound bearing a hydrophobic group and an anionic group capable of binding with a cationic component present in the leukocytes to give morphological differences among the leukocytes;

(c) a buffer for adjusting pH into a range of approximately 2-8.

By the classification of leukocytes, it is intended to classify leukocytes into five groups corresponding to lymphocytes, monocytes, neutrophils, eosinophils, and basophils, respectively.

In one embodiment, the cationic surfactants are quaternary ammonium salt-type cationic surfactants.

According to another specific embodiment, the cationic surfactants are quaternary ammonium salt-type cationic surfactants having a structure represented by the following formula:

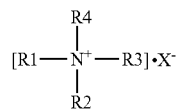

wherein R1 is a $C_6$-$C_{16}$-alkyl or -alkenyl group, R2 and R3 each independently are a $C_1$-$C_4$-alkyl or -alkenyl group, R4 is a $C_1$-$C_4$-alkyl or -alkenyl group or a benzyl group; and X is a halogen.

In one embodiment, the hydrophobic group on the organic compound is selected from an aromatic group, a hydrocarbon group having six or more carbon atoms or a heterocyclic ring having more than 6 carbon atoms, and the anionic group is selected from a carboxyl or sulfonate group.

In one embodiment, the organic compound is an acidic pigment.

The reagent may further include alcohols in an amount of approximately 0.1-10% by volume of the reagent.

In one embodiment, the alcohol may be methanol, ethanol, isopropanol, n-butanol or 2-phenoxyethanol.

The present disclosure also provides a method for classifying leukocytes. The method includes the steps of adding the above defined reagent to a blood sample and then measuring the cell size information and the information on the morphological features.

Specifically, in one embodiment, the method comprises mixing the reagent for classification of leukocytes with the blood sample at a ratio of approximately 10:1-100:1 for approximately 12-30 seconds at a temperature of approximately 10-40° C., and then measuring the cell size information with a low angle scattered light of approximately 1°-5° and measuring the information on the morphological features with a high angle scattered light of approximately 6°-20°.

The reagents and methods disclosed classify leukocytes into five groups in the same channel, each group respectively corresponding to lymphocytes, monocytes, neutrophils, eosinophils, and basophils, whilst erythrocytes are lysed rapidly. With the reagents and methods disclosed, it is also suitable to carry out the classification of leukocytes not only at room temperature, but also at a temperature in a broad range of approximately 10-40° C., significantly extending the range of applicable temperature compared to conventional methods. On the other hand, conducting the classification above the room temperature not only improves the classification reliability and stability by eliminating the influences of the environmental temperature, but also lowers the equipment costs through the omission of cooling devices. With the reagents and methods disclosed, the equipment costs may be further lowered since classification of leukocytes into five groups can be achieved through detection of the scattered light signals at merely two angles.

One embodiment of a reagent for classification of leukocytes includes:

(a) at least two cationic surfactants capable of lysing erythrocytes and partly damaging the cell membrane of leukocytes;

(b) at least one organic compound bearing a hydrophobic group and an anionic group, which is capable of binding with a cationic component present in the leukocytes to give morphological differences among the leukocytes;

(c) a buffer for adjusting pH into a range of approximately 2-8.

The above reagent for classification of leukocytes into five groups can be added into a whole blood sample to classify the leukocytes into five groups corresponding to lymphocytes, monocytes, neutrophils, eosinophils, and basophils and count each of the five groups by measuring the cell size information and the information on morphological features.

In one embodiment, the cationic surfactants are quaternary ammonium salt-type cationic surfactants.

In some embodiments the cationic surfactants are quaternary ammonium salt-type cationic surfactants having a structure represented by the following formula:

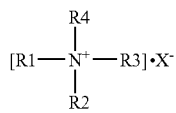

wherein R1 is a $C_6$-$C_{16}$-alkyl or -alkenyl group, R2 and R3 each independently are a $C_1$-$C_4$-alkyl or -alkenyl group, R4 is a $C_1$-$C_4$-alkyl or -alkenyl group or a benzyl group; and X is a halogen.

The cationic surfactant may be used in an amount sufficient to lyse erythrocytes and to partly damage the cell membrane of leukocytes. Specifically, it is usually suitable to use approximately 100-10000 mg/L, such as approximately 200-6000 mg/L, or alternatively, approximately 500-5000 mg/L cationic surfactant, although this amount can be suitably modified depending upon the particular type of surfactant used. Some kinds of surfactants and the optimal amounts thereof are set forth in Table 1. Any combination of two or more of these surfactants may be used accordingly.

TABLE 1

Optimal amount of some surfactants

| Surfactants | Approximate Optimal amount (mg/L) |
| --- | --- |
| Octyltrimethyl ammonium chloride (OTAC, PTI) | 500-5000 mg/L |
| Octyltrimethyl ammonium bromide (OTAB, PTI) | 500-4500 mg/L |
| Decyltrimethyl ammonium chloride (DTAC, PTI) | 200-4000 mg/L |
| Decyltrimethyl ammonium bromide (DTAB, PTI) | 200-3000 mg/L |
| Lauryltrimethyl ammonium chloride (LTAC, PTI) | 100-2000 mg/L |
| Lauryldimethylbenzyl ammonium chloride (DDBAC, PTI) | 100-2000 mg/L |
| Lauryltrimethyl ammonium bromide (LTAB, PTI) | 100-2000 mg/L |
| Lauryldimethylethyl ammonium bromide (EDDAB, PTI) | 100-2000 mg/L |
| Lauryltriethyl ammonium bromide (DTEAB, PTI) | 100-2000 mg/L |
| Myristyltrimethyl ammonium chloride (MTAC, PTI) | 50-1000 mg/L |
| Myristyltrimethyl ammonium bromide (MTAB, PTI) | 50-1000 mg/L |
| Cetyltrimethyl ammonium chloride (CTAC, PTI) | 50-500 mg/L |
| Cetyltrimethyl ammonium bromide (CTAB, PTI) | 50-500 mg/L |

Any combination of surfactants can be used as long as the hemolytic activity thereof is sufficient to create pores in the cell membrane of leukocytes so as to make it possible for cytoplasm to overflow and an organic compound to enter. The surfactants may be used in an amount far less than the amount for lysing the cell membrane so as to completely expose the cell nuclei. The hemolytic activity of the surfactant is in proportion to the chain length of R1. Typically, the more the carbon atoms, the higher hemolytic activity they will have.

In addition to the surfactants, the reagent may further contain an organic compound capable of binding with the cations present in the leukocytes to give morphological differences among leukocyte categories. Such an organic compound bears a hydrophobic group (such as an aromatic group, a hydrocarbon group having six or more carbon atoms and a heterocyclic ring having more than 6 carbon atoms) and an anionic group (such as carboxyl, sulfonate group, and the like), and is negatively charged in an aqueous solution and capable of binding with leukocytes to change the morphological features of leukocytes. Almost all kinds of acidic pigments can be used, such as Acid Blue series, Direct Blue, Acid Green, Acid Yellow, Methyl Red, Methyl Orange, Aniline Blue, Alzarin Yellow and the like. The amount used ranges from 10 to 1000 mg/L, such as from 20 to 500 mg/L.

According to one embodiment, the reagent for classification of leukocytes further contains a buffer for adjusting pH value. Typically, there is no particular limitation on the buffer. Any buffer system commonly used in the art, such as formate, phthalate, acetate, phosphate, TRIS, borate, carbonate, and the like, may be used. The buffer is typically used in an amount ranging from approximately 5-100 mM to adjust the pH of the reagent within the range of approximately 2-8.

Additionally, the reagent may further contain alcohol(s) as a solubilizer. There is no particular limitation on the types of the alcohols that may be used. Exemplary useful alcohols may be methanol, ethanol, isopropanol, n-butanol, 2-phenoxyethanol and the like. The amount of the alcohols, as a solubilizer, typically ranges from 0.1% to 10% by volume of the reagent.

An exemplary method for classifying leukocytes includes the steps of: measuring the cell size information and the information on the morphological features after the reagent has been added to the blood sample and mixed for a period of time, and then classifying the leukocytes into five groups each corresponding to lymphocytes, monocytes, neutrophils, eosinophils, or basophils, and simultaneously counting each of the five groups of cells with a measuring system.

There is no particular limitation on the ratio between the reagent and the blood sample. Typically, it is suitable that the ratio between the blood sample and the reagent is in a range of from approximately 1:10-1:100, and the measurement may be carried out after they have been mixed for approximately 12-30 seconds.

It is suitable to carry out the classification of leukocytes at a temperature in the range of approximately 10-40° C. As long as the temperature is kept at a constant temperature within the range, the stability of the classification result for each test can be ensured. In some embodiments it is desirable to keep the temperature at 35° C. since such a temperature is above the room temperature, making it possible to provide a constant temperature with only a heating device in the practical application. The omission of a cooling device results in a significant saving of the equipment costs.

According to the present disclosure, it is possible to classify leukocytes into five groups within one channel. A laser detecting method may be used for the measurement of the cell size information and the information on the morphological features. Such a method can be carried out by any devices known in the art, using low angle scattered light of approximately 1°-5° for measuring the cell size information and high angle scattered light of approximately 6°-20° for the information on the morphological features. An exemplary device is described in CN 95115317.X, or any others known in the art can be used. The detection of scattered light may also be performed with commonly used photodiode sensors.

The present disclosure will now be described in more detail with reference to the following examples.

EXAMPLE 1

A reagent for classifying leukocytes into five groups was prepared, which included:

| | |
|---|---:|
| Phthalic acid | 1 g |
| 2-phenoxyethanol | 2.5 g |
| Decyltrimethyl ammonium chloride | 3.5 g |
| Octyltrimethyl ammonium bromide | 1.75 g |
| Toluidine blue | 0.025 g |
| Water | to 1 L |
| pH | 4.6 |

The pH value of the reagent according to the above formulation was adjusted to 4.6.

Figure 2:
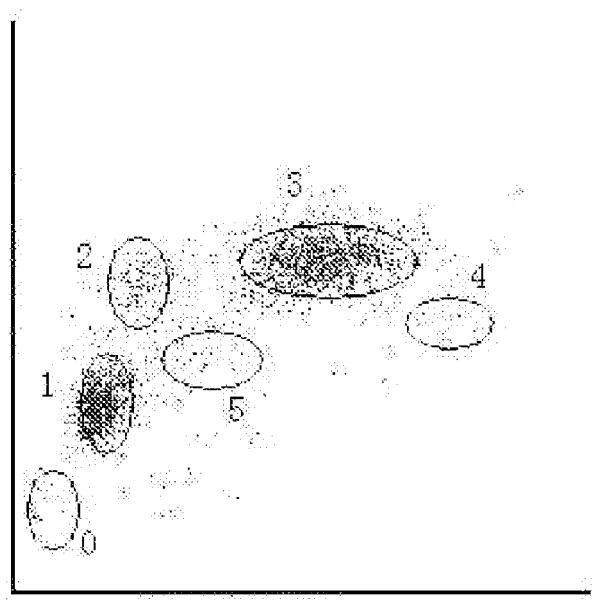
Figure 3:
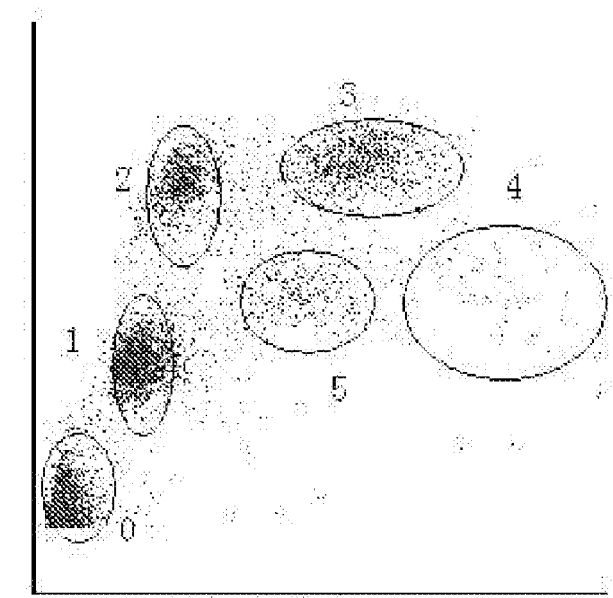

1 mL of the above reagent was added into 10 μl blood at a temperature maintained at 35° C. The leukocytes were tested by a laser detecting method after being mixed for 15 seconds. Low angle scattered light of approximately 1°-5° was used to measure the cell size information and high angle scattered light of approximately 6°-20° was used to measure the information on morphological features. The above reagent was used to treat three blood samples and the results are shown in FIGS. 1, 2 and 3, respectively. It is shown that the leukocytes are classified into five groups each corresponding to lymphocytes, monocytes, neutrophils, eosinophils, and basophils.

EXAMPLE 2

A reagent for classifying leukocytes into five groups was prepared, which included:

| | |
|---|---:|
| sodium dihydrogen phosphate | 0.6 g |
| Disodium phosphate | 4.77 g |
| Methanol | 8 g |
| Lauryltrimethyl ammonium chloride | 0.5 g |
| Octyltrimethyl ammonium bromide | 3 g |
| Acid Blue | 0.05 g |
| water | to 1 L |
| pH | 7.5 |

The pH value of the reagent according to the above formulation was adjusted to 7.5.

Figure 4:
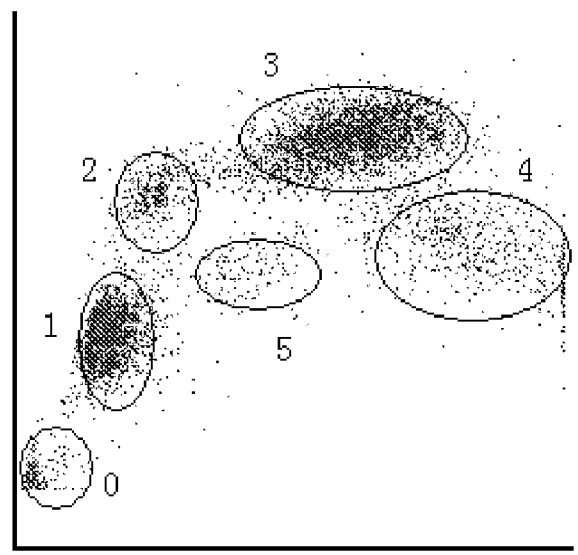
FIG. 4 shows the classification of leukocytes into five groups with another embodiment of a reagent for classification of leukocytes.

1 mL of the above reagent was added into 10 μl blood at a temperature maintained at 35° C. The leukocytes were tested by a laser detecting method after being mixed for 15 seconds. Low angle scattered light of approximately 1°-5° was used to measure the cell size information and high angle scattered light of approximately 6°-20° was used to measure the information on morphological features. The result is shown in FIG. 4, in which the leukocytes are classified into five groups each corresponding to lymphocytes, monocytes, neutrophils, eosinophils, and basophils.

EXAMPLE 3

A reagent for classifying leukocytes into five groups was prepared, which included:

| | |
|---|---:|
| Formic acid | 1.5 g |
| Glycine | 1 g |
| Isopropanol | 10 g |
| Lauryldimethylbenzyl ammonium chloride | 0.2 g |
| Octyltrimethyl ammonium chloride | 3 g |
| Methyl red | 0.05 g |
| water | to 1 L |
| pH | 2.8 |

The pH value of the reagent according to the above formulation was adjusted to 2.8.

Figure 5:
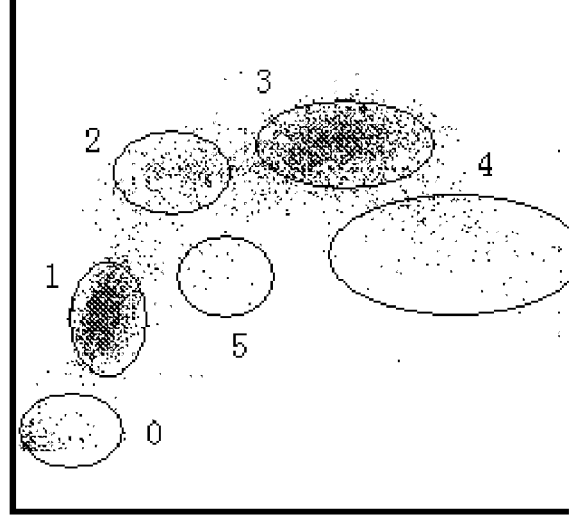
FIG. 5 shows the classification of leukocytes into five groups with yet another embodiment of a reagent for classification of leukocytes.

1 mL of the above reagent was added into 10 μl blood at a temperature maintained at 35° C. The leukocytes were tested by a laser detecting method after being mixed for 15 seconds. Low angle scattered light of approximately 1°-5° was used to measure the cell size information and high angle scattered light of approximately 6°-20° was used to measure the information on morphological features. The result is shown in FIG. 5, in which the leukocytes are classified into five groups each corresponding to lymphocytes, monocytes, neutrophils, eosinophils, and basophils.

While the present disclosure is described in detail with reference to particular embodiments, the present invention is not to be construed in any case as being limited to these embodiments. It will be appreciated that various modifications may be made without departing from the spirit and scope of the invention and thus are considered as within the scope of the present invention.

What we claim is:

1. A reagent for classification of leukocytes, the reagent comprising:
   (a) at least two cationic surfactants capable of lysing erythrocytes and partly damaging the cell membrane of leukocytes;
   (b) at least one organic compound bearing a hydrophobic group and an anionic group capable of binding with a cationic component present in the leukocytes to give morphological differences among the leukocytes; and
   (c) a buffer for adjusting pH into a range of between approximately 2-8,
   wherein the at least two cationic surfactants are each independently quaternary ammonium salt-type cationic surfactants having a structure represented by the following formula

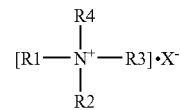

wherein R1 is a $C_6$-$C_{16}$-alkyl or -alkenyl group, R2 and R3 each independently are $C_1$-$C_4$-alkyl or -alkenyl group, R4 is a $C_1$-$C_4$-alkyl or -alkenyl group or a benzyl group, and X is a halogen; and
   wherein the reagent is configured to classify leukocytes into five groups corresponding to lymphocytes, monocytes, neutrophils, eosinophils, and basophils.

2. The reagent for classification of leukocytes according to claim 1, wherein the hydrophobic group on the organic compound is selected from: an aromatic group, a hydrocarbon group having six or more carbon atoms or a heterocyclic ring having more than 6 carbon atoms; and the anionic group on the organic compound is a carboxyl group or a sulfonate group.

3. The reagent for classification of leukocytes according to claim 1, wherein the organic compound is an acidic pigment.

4. The reagent for classification of leukocytes according to claim 1, wherein the reagent comprises an alcohol in an amount of between approximately 0.1-10% by volume of the reagent.

5. The reagent for classification of leukocytes according to claim 4, wherein the alcohol is chosen from at least one of: methanol, ethanol, isopropanol, n-butanol or 2-phenoxyethanol.

6. The reagent for classification of leukocytes according to claim 1, wherein R1 is a $C_6$-$C_{16}$-alkyl group, R2 and R3 each independently is a $C_1$-$C_4$-alkyl group, R4 is a $C_1$-$C_4$-alkyl or a benzyl group; and X is a halogen.

7. The reagent for classification of leukocytes according to claim 6, wherein the cationic surfactants are selected from at least one of the following: octyltrimethyl ammonium bromide, octyltrimethyl ammonium chloride, decyltrimethyl ammonium chloride, laureltrimethyl ammonium chloride, and lauryldimethylbenzyl ammonium chloride.

8. A method for classifying leukocytes, comprising:
   obtaining a reagent comprising:
   (a) at least two cationic surfactants capable of lysing erythrocytes and partly damaging the cell membrane of leukocytes;
   (b) at least one organic compound bearing a hydrophobic group and an anionic group capable of binding with a cationic component present in the leukocytes to give morphological differences among the leukocytes; and
   (c) a buffer for adjusting pH into a range of approximately 2-8;
   mixing the reagent with a blood sample;
   measuring cell size information and information on morphological features of the leukocytes, and
   classifying the leukocytes into five groups corresponding to lymphocytes, monocytes, neutrophils, eosinophils, and basophils.

9. The method according to claim 8, wherein mixing the reagent with the blood sample comprises:
   mixing the reagent and the blood sample at a ratio of approximately 10:1-100:1 for between approximately 12-30 seconds at a temperature of between approximately 10-40° C.

10. The method according to claim 9, wherein measuring the cell size information comprises measuring cell size information with a low angle scattered light of approximately between 1°-5°; and wherein measuring the information on morphological features comprises measuring information on morphological features with a high angle scattered light of approximately between 6°-20°.

11. The method according to claim 8, wherein obtaining a reagent comprises obtaining a reagent that includes cationic surfactants which are quaternary ammonium salt-type cationic surfactants.

12. The method according to claim 11, wherein the cationic surfactants are quaternary ammonium salt-type cationic surfactants having a structure represented by the following formula:

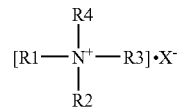

wherein R1 is a $C_6$-$C_{16}$-alkyl or -alkenyl group, R2 and R3 each independently are a $C_1$-$C_4$-alkyl or -alkenyl group, R4 is a $C_1$-$C_4$-alkyl or -alkenyl group or a benzyl group; and X is a halogen.

13. The method according to claim 12, wherein R1 is a $C_6$-$C_{16}$-alkyl group, R2 and R3 each independently is a $C_1$-$C_4$-alkyl group, R4 is a $C_1$-$C_4$-alkyl or a benzyl group; and X is a halogen.

14. The method according to claim 13, wherein the cationic surfactants are selected from at least one of the following: octyltrimethyl ammonium bromide, octyltrimethyl ammonium chloride, decyltrimethyl ammonium chloride, laureltrimethyl ammonium chloride, and lauryldimethylbenzyl ammonium chloride.

15. The method according to claim 8, wherein the hydrophobic group on the organic compound is selected from: an aromatic group, a hydrocarbon group having six or more carbon atoms or a heterocyclic ring having more than 6 carbon atoms; and the anionic group on the organic compound is a carboxyl group or a sulfonate group.

16. The method according to claim 8, wherein the organic compound is an acidic pigment.

17. The method according to claim 8, wherein the reagent comprises an alcohol in an amount of approximately between 0.1-10% by volume of the reagent.

18. The method according to claim 17, wherein the alcohol is chosen from at least one of: methanol, ethanol, isopropanol, n-butanol or 2-phenoxyethanol.

* * * * *